United States Patent [19]

Auerbach

[11] 4,164,227
[45] Aug. 14, 1979

[54] RATE FAILURE INDICATOR

[75] Inventor: Albert A. Auerbach, New York, N.Y.

[73] Assignee: Medalert Corporation, New York, N.Y.

[21] Appl. No.: 946,079

[22] Filed: Sep. 27, 1978

[51] Int. Cl.² .............................................. A61N 1/36
[52] U.S. Cl. ........................................... 128/419 PT
[58] Field of Search .................. 128/419 PG, 419 PT

[56] References Cited

U.S. PATENT DOCUMENTS

| | | | |
|---|---|---|---|
| 3,612,041 | 10/1971 | Ragsdale | 128/2.06 A |
| 3,742,937 | 7/1973 | Manuel et al. | 128/2.06 A |
| 3,782,367 | 1/1974 | Hochberg et al. | 128/2.06 A |
| 3,832,994 | 9/1974 | Bicher et al. | 128/2.06 A |
| 4,018,219 | 4/1977 | Hojaiban | 128/2.06 A |
| 4,055,189 | 10/1977 | Auerbach et al. | 128/419 PG |
| 4,088,139 | 5/1978 | Auerbach | 128/419 PT |
| 4,096,865 | 6/1978 | Auerbach et al. | 128/419 PT |

Primary Examiner—William E. Kamm
Attorney, Agent, or Firm—S. C. Yuter

[57] ABSTRACT

A device for automatically indicating a rate failure condition in a pacer monitoring the intrinsic pacer rate in both demand and fixed rate modes, including a first limit circuit preset at a low level of activity coupled to the monitoring means, and a second limit circuit preset at a high level of activity coupled to the monitoring means. A first switch is connected to the first limit circuit, and a second switch is connected to the second limit circuit. The first limit circuit responds to the combined rate of pacer and spontaneous activity falling below a preset level by placing the first switch in a switched condition, and the second limit circuit responds to the rate of pacer activity exceeding a preset level by placing the second switch means in a switched condition. Indicating means converts the switched conditions to distinguishable marking pulse signal for later clinical electrocardiogram detection.

15 Claims, 7 Drawing Figures

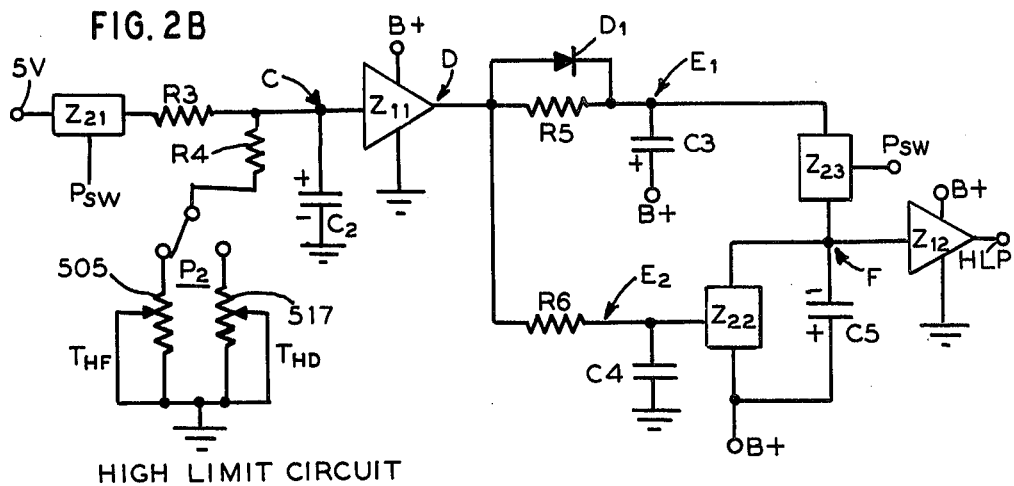
FIG. 2B HIGH LIMIT CIRCUIT
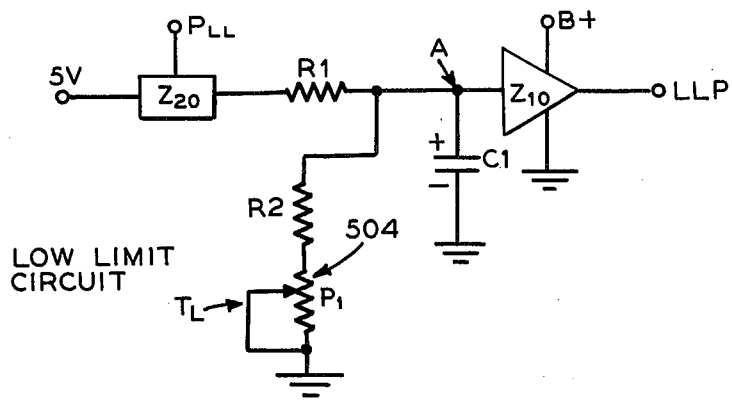
FIG. 2A LOW LIMIT CIRCUIT
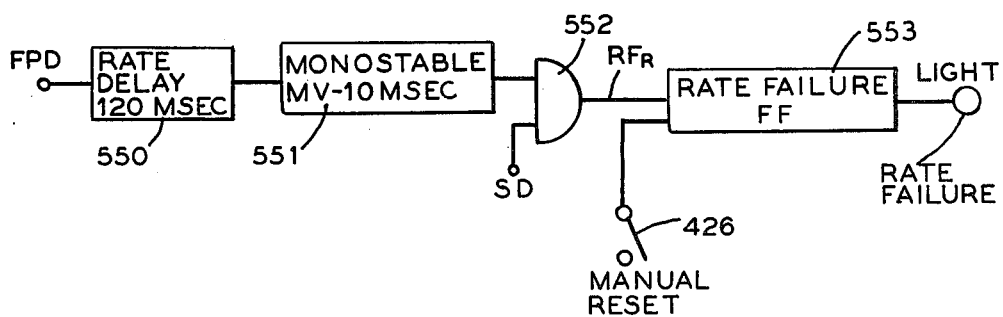
FIG. 4

ABNORMAL RATE MARKER TIMING
1. LOW RATE MARKERS

ABNORMAL RATE MARKER (CONT'D)
2. HIGH RATE MARKERS (DEMAND OR FIXED RATE)

Figure 1:
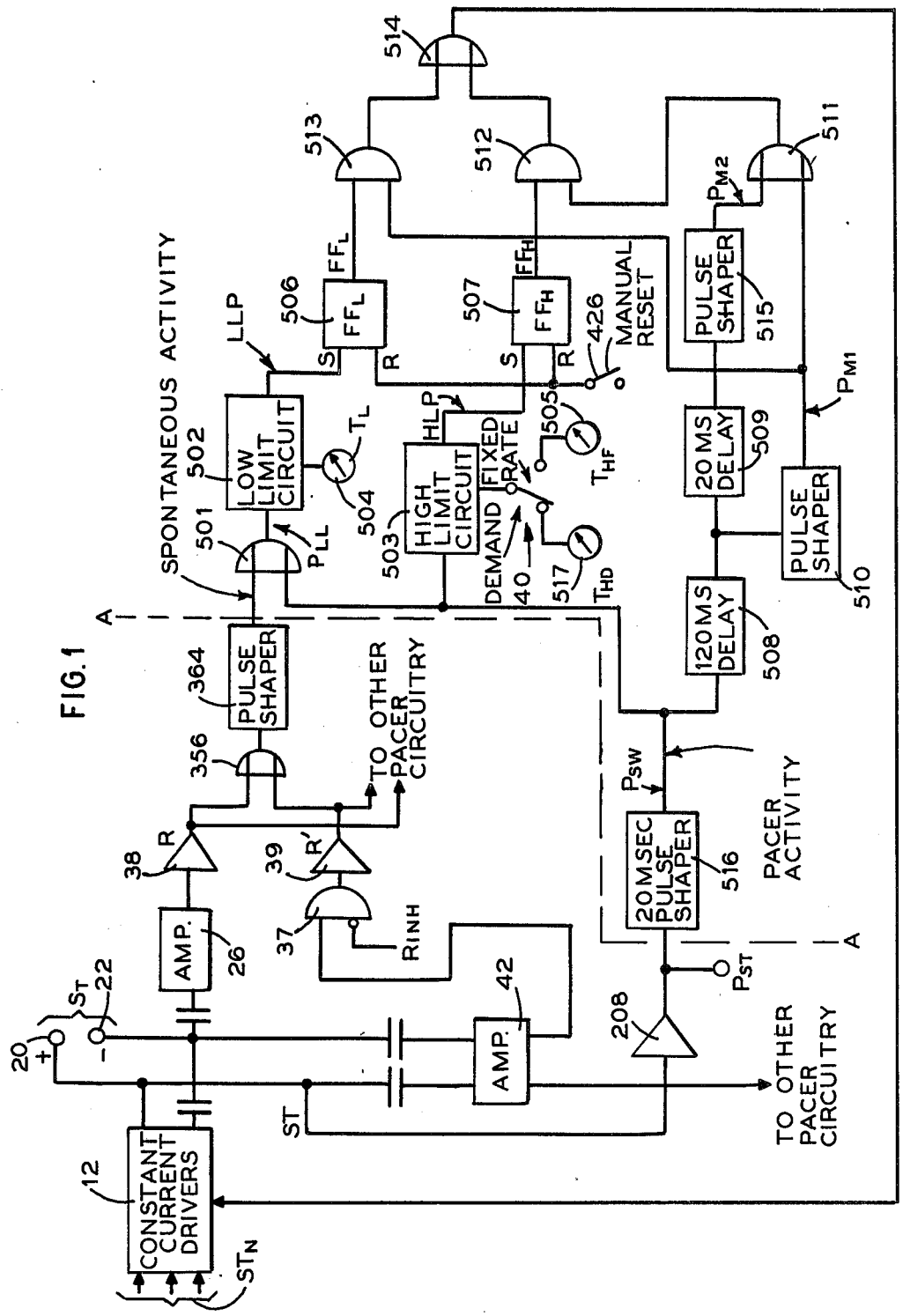

FIG. 3C
1. LOW LIMIT TIMING
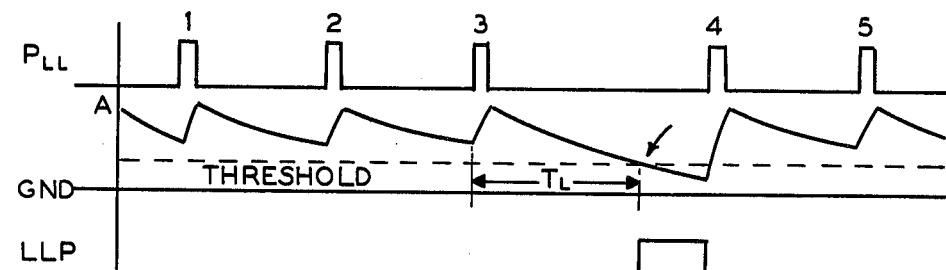
2. HIGH LIMIT TIMING (DEMAND OR FIXED RATE)
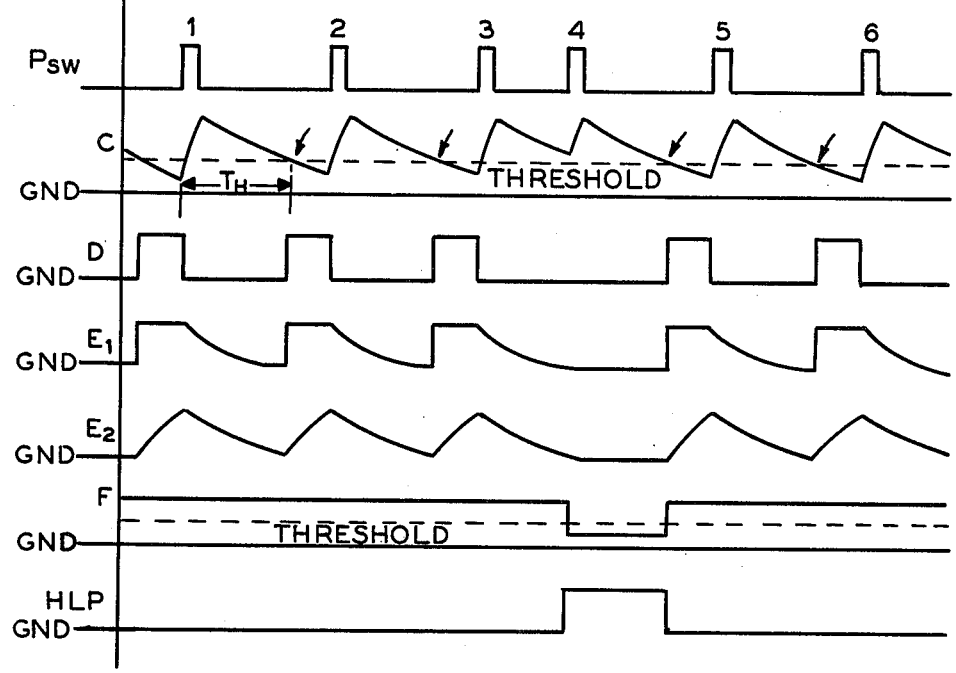

RATE FAILURE INDICATOR

This invention relates to monitoring cardiac pacers, and more particularly to monitoring cardiac pacers in which marker pulses are superimposed on a patient's electrocardiogram to indicate both rate changes and prior failures of the pacer to properly stimulate the heart or properly sense its spontaneous activity.

The clinical significance of a rate change indication is that it permits the diagnosis of incipient pacer failure even though the pacer has retained its ability to properly stimulate and sense, i.e., is otherwise functioning normally. The rate change usually indicates a potential battery or electronic problem, but this clinical indication is lost in those cases in which, despite occasional tests, the patient's "rate history" is missing or is never kept. Since the clinician consequently does not know the pacer initial rate setting, he simply observes that the pacer is functioning normally and remains unaware of the problem.

Under these conditions, it is the purpose of this invention to protect the pacer patient from possible pacer failure by taking advantage of the fact that if a single battery in the pacer has failed or is on the verge of failing, the pacer rate normally drops by 3 to 10 beats per minute. Conversely, the rate may increase 3 to 10 beats per minute above the original preset rate if various electronic failures occur prior to a potentially dangerous "runaway". This invention provides an "automatic rate history", in the sense that a special set of rate markers is automatically generated under either of the two conditions above, thereby informing the clinician that the pacer rate is abnormal. Information is thereby provided which will facilitate the detection of incipient battery depletion or electronic "runaways". The mode of generation of these markers is described below.

Pacer which provide markers are described in prior U.S. Pat. No. 4,096,865 issued June 27, 1978, and No. 4,088,139 issued May 9, 1978, the disclosures of which are hereby specifically incorporated by reference.

One form of failure not detected directly by the aforesaid U.S. patents is change in intrinsic rate. As stated above, this measurement is a valuable tool in enabling clinicians to derive information from an electrocardiogram.

It is therefore the object of this invention to provide a novel and unique system for monitoring cardiac pacers which will provide a physical indication of a change in rate above or below predetermined limits.

It is another object of this invention to provide a novel and unique system for placing a discernible mark on an electrocardiogram indicating a change in pacer rate above or below a predetermined rate.

In accordance with the foregoing objects, the present invention provides an additional set of marker pulses which is used to indicate that the intrinsic rate of the pacer is beyond a preset high limit or low limit. In the context of the aforementioned U.S. patents, the additional marker pulses are distinguished from the marker pulses already present, which indicate "failure to capture" or "failure to sense", by their occurrence at different times with respect to the cardiac pacer stimulus than the times of occurrence of the capture and sensing failure marker pulses. By way of specific example, in said prior patents, failure to capture can be indicated on the cardiogram by a marker pulse 40 msec after the pacer stimulus, and failure to sense by a marker pulse 80 msec after the stimulus. Thus, abnormal rate changes can be indicated by either single or double marker pulses 120 msec after the pacer stimulus. A pair of pulses, separated by 20 msec, the first of which starts 120 msec after the pacer stimulus, can be used to indicate an abnormal rate increase; a single pulse, 120 msec after the pacer stimulus, can be used to indicate an abnormal rate decrease. Of course, other variations of the rate change marker will be within the scope of the invention and evident to those skilled in the art. The desired result is only to provide clinical measurability of the rate change effect by a desirable physical indicator such as a mark on an electrocardiogram.

Figure 3A:
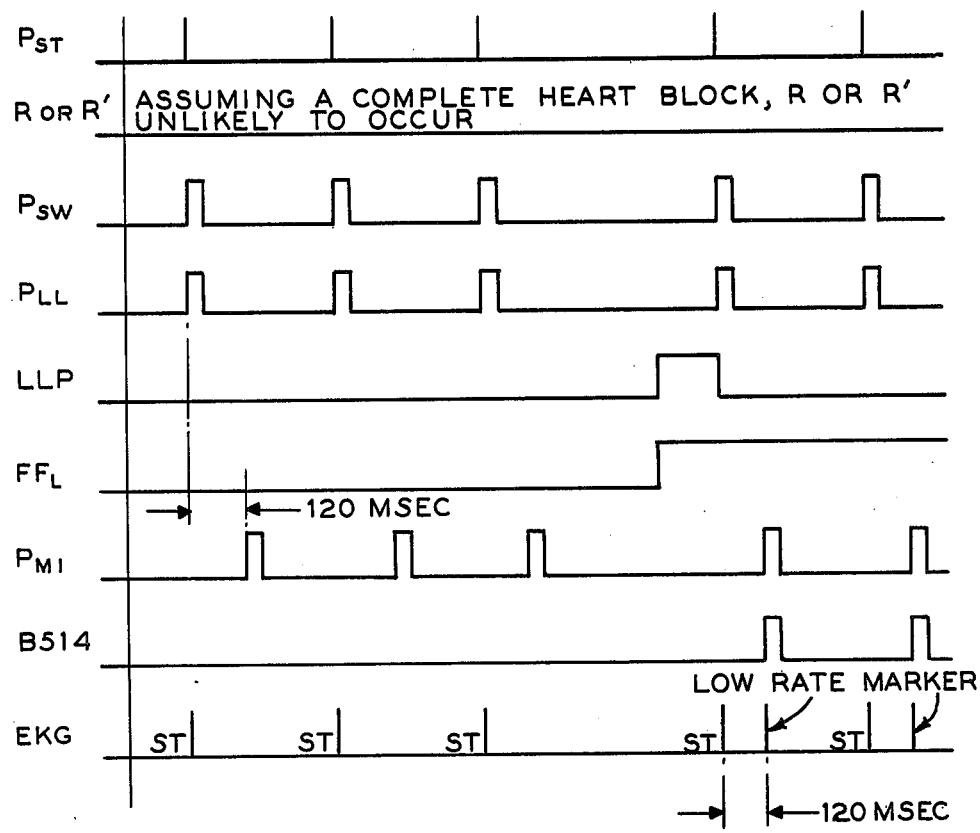
Figure 3B:
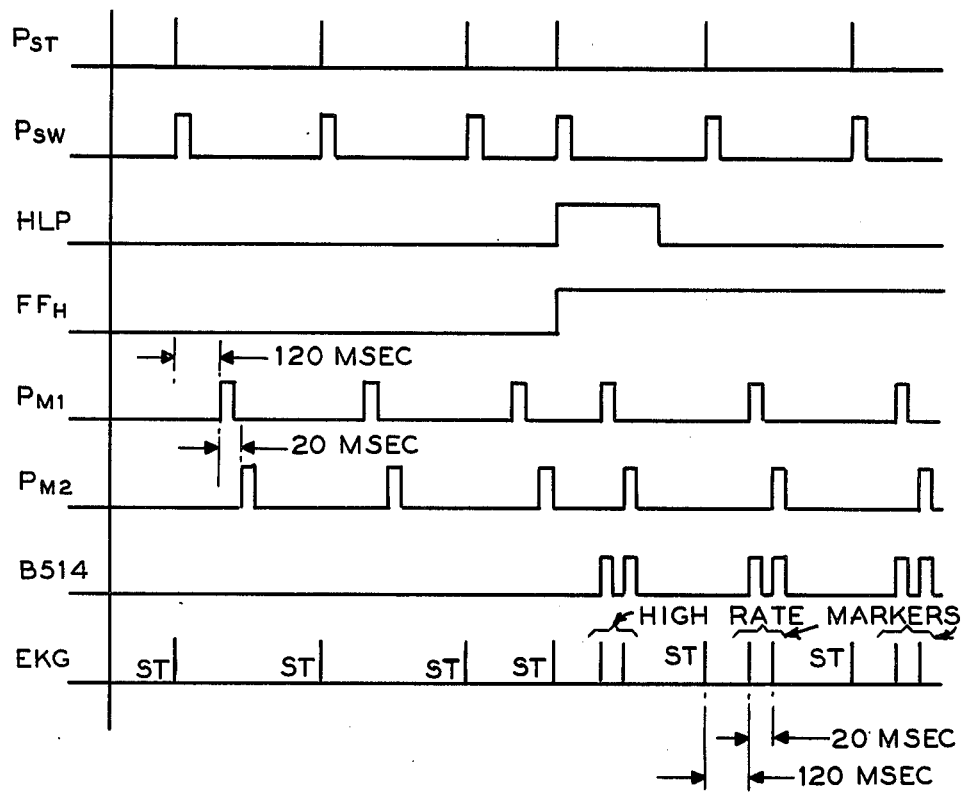

The foregoing objects and brief description will become more apparent from the following more detailed description and appended drawings, wherein:

FIG. 1 illustrates a block diagram of the invention showing integration of the inventive concept with a pacer;

FIGS. 2A and 2B detail a specific low limit circuit and a specific high limit circuit;

FIGS. 3A, 3B and 3C are timing diagrams illustrating the signal relationship at various points throughout the circuit; and FIG. 4 shows a remote rate failure detecting circuit.

Referring now to FIG. 1, the rate marking concept is shown in conjunction with a pacer circuit. The specific components of the pacer circuit are shown to the left of line A—A. For ease of illustration, the components shown are derived from a patent specification already noted above, for example, U.S. Pat. No. 4,088,139, and the reference numbers are also corresponding. The disclosure of the U.S. Pat. No. 4,088,139 is specifically incorporated by reference for this purpose herein. The pacer stimulating electrodes 20 and 22 are driven in accordance with various signals applied to the constant current drivers 12. As set forth in U.S. Pat. No. 4,088,139, the existence of certain conditions will cause certain stimulating or marking signals to be applied to the drivers 12 along inputs designated $ST_n$, resulting in discernible markings on a monitoring electrocardiogram. The purpose of this invention is to monitor the natural or stimulated heart activity, or both, and to provide a physical indication of a defined abnormality, i.e., high or low rate. As a best mode, such an indication can be provided in conjunction with the marking monitor described in the aforesaid U.S. patents by the provision of additional rate failure marking signals supplied to the drivers 12.

In accordance with this concept, the pacer electrodes 20 and 22 both stimulate and sense, sensed signals being provided to amplifiers 26 and 42, and then to other pacer circuitry for generation of the $ST_n$ signals, all as described in the aforesaid U.S. patent. Amplifiers 38 and 39 produce an R and R' signal respectively.

The timing relationships between the components in FIG. 1 are illustrated in FIGS. 3A and 3B. Buffer 356, switch 40 and pulse shaper 364 specify elements in the aforesaid U.S. patent. The output of pulse shaper 364 provides pulses which correspond to, i.e. are generated only by, the spontaneous activity of the heart. $P_{SW}$ is a 20 millisecond pulse which is generated by pulse shaper 516 each time that a pacer stimulus ($P_{ST}$) is released. As determined by the specific pacer design, $P_{SW}$ may occur at only one "intrinsic" rate, independent of whether the pacer is in its "demand" mode or in a "fixed rate" test mode. In some designs, however, the fixed test rate is higher than the intrinsic demand rate. The more general case of two different operating rates is illustrated, in which one of two possible high rate limits is selected by element 40 depending on whether the pacer is in its "fixed rate" or "demand" operating mode. In this manner, a rate measuring circuit which corresponds to the operating mode of the pacer may be used. For the high limit measurement, circuit 503 is used subject to the condition imposed by switch 40. $P_{SW}$ then provides an input to 503 at a rate which cannot be exceeded without an indication of abnormal operation being given. Similarly, $P_{SW}$ and the output of pulse shaper 364 are inputs to buffer 501. The object of providing this particular buffed signal to low limit circuit 502 is to provide a signal source, combining both spontaneous and pacer stimuli activity, which must occur at some minimum rate below which activity of the pacer will be judged to be abnormal.

Low limit circuit 502 (further detailed below) is designed to provide a low limit pulse (LLP) at a time shortly after the pacer rate has fallen below the specified limit. The limit is selected by adjustment 504 (labeled $T_L$). Correspondingly, when the rate of occurrence of $P_{SW}$ exceeds one of the specified high limits, the high limit pulse HLP is generated. These limits are specified by adjustments 505 (labeled $T_{HF}$) in the fixed rate mode and 517 (labeled $T_{HD}$) in the demand mode. All of these adjustments may be made prior to installation of the pacer. LLP, if generated, sets FF 506. HLP, if generated, sets FF 507. These circuits provide signals $FF_L$ and $FF_H$ respectively, and these signals will continue to be present, i.e, both flip flops will remain set, after any rate variation which takes the pacer rate beyond the limits specified by 504 and 505 or 517. They remain in this state until manually reset by a device used only in the clinician's office. This is identical to the practice which would also be required to reset the marker indications produced when either "failure to capture" or "failure to sense" occurs as noted in the aforesaid U.S. patents.

The abnormal rate indications $FF_L$ and $FF_H$ are now used to control delayed $P_{ST}$ pulses. Signal $P_{SW}$ triggers a 120 msec delay element 508 which generates a pulse, which is then shaped by pulse shaper 510 to produce $P_{M1}$. The output of 508 also triggers a 20 msec delay element 509. Delay element 509 generates a pulse 20 msec after $P_{M1}$, and the output of delay element 509 is in turn applied to pulse shaper 515 to produce the signal $P_{M2}$. Signal $P_{M1}$ is applied to gate 513 which is controlled by the low limit signal $FF_L$. An output from gate 513 will be present 120 msec after any pacer stimulus which is released subsequent to the occurrence of a low limit failure.

Signals $P_{M1}$ and $P_{M2}$ are buffed together by buffer 511, whose output is applied to gate 512. The output of gate 512 will be present only subsequent to occurrence of the high limit failure. The output of gate 512 is obviously a double pulse, the first of which occurs 120 msec after any evoked stimulus and the second 20 msec later. The outputs of the high limit gate 512 and the low limit gate 513 are now buffed together by buffer 514 and applied to the constant current driver 12 as shown in FIG. 1.

The details of the high and low limit circuits as well as their timing diagrams are now described.

Reference should now be made to FIGS. 2A and 2B. Signal $P_{LL}$ is a pulse of standard width taken from the output of buffer 501, and, as noted above, combines both spontaneous activity and pacer stimuli. $P_{SW}$ is also a pulse of standard width which occurs synchronously with and is initiated by, each pacer stimulus, at one of two possible rates. $Z_{20}$ is a Field Effect Transistor (FET) switch. In the presence of an input pulse, the FET provides a very low resistance connection between its source (input) and sink (output). $Z_{20}$ is the only FET in the low limit circuit. The high limit circuit contains FET switches $Z_{21}$, $Z_{22}$ and $Z_{23}$. There are in addition three "inverters", $Z_{10}$, $Z_{11}$ and $Z_{12}$, which are used in the high and low limits circuits, as shown. The inverter has two states: when its input is above a given threshold, its output is low, usually at ground potential; conversely, when the input is below a given threshold, the output is high (at B+). The remaining elements used are resistors, capacitors, one diode, and two variable resistors ($P_1$ and $P_2$). $P_1$ (or element 504) controls the low frequency limit; $P_2$ (which may be either element 517 or element 505) controls the high frequency limit.

The timing diagrams in FIGS. 3A, 3B and 3C must now be referred to, together with FIGS. 2A and 2B, in the following description of the operation of the low limit circuit. When signal $P_{LL}$ is applied to FET $Z_{20}$, $Z_{20}$ connects the five volt (5 V) power source to the circuit comprised of elements $R_1$, $R_2$, $P_1$ and $C_1$. Capacitor $C_1$ now charges to approximately five volts during the interval in which $P_{LL}$ is present. After the charging interval, $C_1$ discharges through $R_2$ and $P_1$. The voltage on $C_1$ (labeled A) is shown on the corresponding timing diagram line in FIG. 3C. Note that the signal does not discharge to, i.e. reach, the selected threshold value unless the time between $P_{LL}$ pulses exceeds interval $T_L$ seconds (corresponding to a frequency, in beats per minute, of $60/T_L$). The value of $T_L$ is chosen by appropriately setting $P_1$. However, if A crosses the selected threshold, the output of $Z_{10}$ (LLP) rises to B+ and will stay at that value as long as A remains below the threshold. This condition occurs between the third and fourth $P_{LL}$ pulse. The fourth $P_{LL}$ pulse which follows the abnormally lengthened interval, then restores A to a positive value close to B+, and the $Z_{10}$ output (LLP) drops back to ground level. In summary, LLP starts at a time ($T_L$) following the last normal stimulus and lasts until the next stimulus occurs. Its presence obviously indicates the occurrence of an interval longer than $T_L$, or conversely a frequency lower than the selected low frequency limit.

The upper frequency limit is controlled by the circuit in FIG. 2B, and is further described by the timing diagram (FIG. 3C). Pulse $P_{SW}$ is now applied to FET $Z_{21}$. When $P_{SW}$ is present, the five volt (5 V) power source is applied to the circuit comprised of elements $R_3$, $R_4$, $C_2$ and $P_2$. The voltage on $C_2$ (labeled C) is shown on the timing diagram. C charges and discharges in the manner previously described, but the time constants are now chosen so that C normally crosses a selected threshold. The time required for this crossing is the interval $T_H$ seconds, corresponding to the upper frequency limit ($60/T_H$ in beats per minute). When C crosses the threshold, the output of inverter $Z_{11}$ rises to its maximum level and remains at that level as long as C is below the threshold. C will rise above the threshold as soon as the next $P_{SW}$ occurs. $C_2$ then charges once more and the output of $Z_{11}$ drops down to ground.

At output D a sequence of pulses corresponding to the intervals during which C is below the threshold value, is observed for each of the normally spaced pacer stimuli. If, however, a stimulus is released at a time less than $T_H$ following a normal stimulus, C does not cross the threshold, but is instead restored to a maximum value by $P_{SW}$. Note that D is consequently absent since C remains above threshold. So long as this situation persists, the voltage on D will remain at its ground level.

Referring now to voltages $E_1$ and $E_2$ (the voltages on charging capacitors $C_3$ and $C_4$ respectively), it should be noted that $C_3$ charges quickly through diode $D_1$, whereas $C_4$ charges relatively slowly through resistor $R_6$. Voltage $E_1$ therefore reaches its maximum value well before $E_2$. Capacitor $C_3$ discharges through $R_5$, and $C_4$ discharges through $R_6$. These resistors are also proportioned so that the discharge time of $C_4$ is somewhat longer than the discharge time of $C_3$.

The voltages $E_1$ and $E_2$ are shown on the timing diagram (FIG. 3C) and will normally recur, as indicated, so long as an abnormally early $P_{SW}$ pulse does not occur. It should also be noted that $E_2$ is applied to FET switch $Z_{22}$, and $P_{SW}$ is applied to FET switch $Z_{23}$.

The voltage $E_2$, when present, allows conduction through $Z_{22}$ which effectively shorts $C_5$. The voltage F consequently rises to a value close to $B+$, leaving $C_5$ with effectively zero voltage drop across it. This condition will persist, and F will remain high, so long as no abnormally early pacemaker stimuli occur.

The situation with regard to FET switch $Z_{23}$ is somewhat different. The switch $Z_{23}$, in the presence of $P_{SW}$, provides a conduction path between the junction of the two FET switches (at voltage F) and the midpoint of the network driven by $Z_{11}$ (at voltage $E_1$). Since $E_1$ reaches its maximum value relatively quickly in the presence of $P_{SW}$, and F is normally high, little current normally flows through $Z_{23}$. F consequently remains above the threshold for inverter $Z_{12}$, and the output of inverter $Z_{12}$, which is used to generate the HLP pulse, therefore remains at a correspondingly low ground level.

This stable situation changes when an abnormally early pacer spike is released. Referring to voltage C, note that the occurrence of an early pacer stimulus (the fourth $P_{SW}$ pulse) charges $C_2$ and prevents C from crossing the threshold at its standard time. The corresponding potential change D at the output $Z_{11}$, is therefore absent. Voltages $E_1$ and $E_2$ then both return to their minimum level and do not rise with the occurrence of $P_4$ since C is still above the threshold value. When $P_{SW}$ is now applied to $Z_{23}$, $Z_{23}$ conducts. Since $E_1$ is at a low level, voltage $B+$ will now divide between $C_5$ and $C_3$. This division is in inverse proportion to the values of these capacitors. The capacitor $C_5$ is chosen so that the voltage change at F is sufficiently great to cross the threshold for inverter $Z_{12}$. The output of $Z_{12}$ (HLP) now rises to $B+$ and will stay at that level until a normal time interval (greater than $T_H$) occurs. As illustrated, the next normally timed pulse is the fifth $P_{SW}$ pulse. Consequently, C will have crossed its normal threshold before this pulse occurs. The fifth $P_{SW}$ pulse then produces the previously described voltage changes in D, $E_1$ and $E_2$. The voltage F is simultaneously restored to its high value, and HLP drops to its low value. The HLP pulse, generated in this manner, serves as an indication of an abnormally high pacer stimulus frequency.

It may also be noted at this point that if $C_5$ is doubled, the time interval for voltage F to cross the threshold required for a change in the state of $Z_{12}$, will also double. With appropriate choice of component values, it will then take two consecutive pulses, separated by the selected upper frequency interval, to produce an HLP marker. If the occurrence of a single abnormally short interval is deemed in the future not to be a serious problem, whereas two consecutive short intervals is taken as sufficient cause for marking the electrocardiogram, this circuit option is available. Finally, it is noted that the inverters have the property that their thresholds vary in direct proportion to their $B+$ supply. Selected values of $T_H$ and $T_L$ will consequently remain stable and relatively independent of variations in the value of $B+$.

One additional point to be noted is that $P_1$ (the low frequency limit control) and $P_2$ (the high frequency limit control) can be readily linked to the rate control mechanism of a "rate-programmable" pacer. Thus, whatever rate $(f_v)$ the pacer is programmed for, $f_L = 60/T_L$ (the low frequency limit) and $f_H = 60/T_H$ (the high frequency limit) can be arranged to remain at fixed and constant frequency differences ($\Delta f_L$ and $\Delta f_H$) from the programmed rate, in accordance with the relationships $$\Delta f_L = f_V - f_L$$

$$\Delta f_V = f_H - f_V$$

It is apparent that $f_H$ may have two values, $f_{HD}$ and $f_{HF}$, depending on whether the pacer is in the demand or fixed rate modes respectively.

The foregoing specific circuits are illustrated solely for the purpose of exemplifying operation of the inventive concept herein. It will be understoood that other forms of circuitry may be employed by one skilled in the art to accomplish the rate failure indication function of the present invention. For example, the limit circuits can be counters and comparators with preset high and low limits. In addition, although the concept of rate failure indication has been illustrated with respect to providing spaced marker pulses on an electrocardiogram in conjunction with the marker monitor devices described in the aforesaid U.S. patents, it is possible within the spirit of the invention to provide other forms of discernible indications to warn of the rate failure. Further, the rate failure indication signals can be utilized for long distance transmission as with telephone monitoring or other forms of communication as well as or in addition to providing local alarm or indication.

Further, the present invention may be employable in conjunction with automatic detection of abnormal rate pulses when they are transtelephonically sent to a remote detector (see the aforesaid U.S. Pat. No. 4,088,139). To effect this detection in conjunction with the system of U.S. Pat. No. 4,088,139, as shown in FIG. 4 herein, it is necessary to add to the circuit of FIG. 10 of the said U.S. patent an additional rate delay 550 responsive to a pulse detected signal (FPD; see FIG. 10 of U.S. Pat. No. 4,088,139), a monostable delay 551, a gate 552, and a rate failure flip flop 553. A suitable alarm light 554 can provide the visible rate failure indication. Other variations of course will be evident.

Other modifications, deletions, additions and variations will be evident to those skilled in the art. While the invention has thus been described with reference to a limited number of embodiments, it will be apparent that such other modifications, deletions, additions and variations may be covered by the following claims within the true spirit and scope of the invention.

What is claimed is:

1. An improvement for automatically indicating a rate failure condition in a pacer for pacing monitoring, comprising monitoring means for monitoring the rate of spontaneous and pacer activity of said pacer, first limit means preset at a low level of combined spontaneous and pacer activity coupled to said monitoring means, second limit means preset at a high level of pacer activity coupled to said monitoring means, first switch means connected to said first limit means, second switch means connected to said second limit means, said first limit means responsive to said rate of combined spontaneous and pacer activity falling below said preset low level for placing said first switch means in a switched condition, said second limit means responsive to said rate of activity exceeding said preset high level of pacer activity for placing said second switch means in a switched condition, and indicating means coupled to said first and second switch means for converting said switched conditions to distinguishable marking pulse signals for later clinical electrocardiogram detection.

2. The improvement of claim 1 wherein said first and second switches are manually resettable.

3. The improvement of claim 1 wherein said pacer provides monitoring of failure conditions and said indicating means includes marking means for providing marking pulses discernible on an electrocardiogram for marking the existence of said failure conditions, and wherein said indicating means also includes gating means for coupling said switched conditions to said indicating means for providing a further marking pulse indicative of said switched conditions.

4. The improvement of claim 3 wherein said first and second limit means include delay means for providing a first marking pulse indicative of said rate of activity falling below said preset low level and a second marking pulse indicative of said rate of activity exceeding said preset high level, said first and second marking pulses thereby being informationally distinguishable by virtue of their physical separation on said electrocardiogram.

5. The improvement of claim 1 wherein said indicating means is responsive to a time delay.

6. The improvement of claim 4 wherein said first marking pulse is a single pulse indication and said second marking pulse is a double pulse indication.

7. An improvement for automatically indicating a rate failure condition in a pacer comprising marking means for generating a plurality of marker pulses, said marker pulses being coupled to the electrodes of said pacemaker and thereby clinically discernible on an electrocardiogram, sensing means coupled to said electrodes for detecting the rate of both natural and pacer activity and providing electrical pulses corresponding thereto, buffering means coupled both of said natural and pacer series of pulses to a low limit circuit, said low limit circuit having a preset threshold of low rate detection and providing an output signal when the input thereto falls below said low limit, a high limit circuit responsive to said pacer pulses, said high limit circuit having a preset threshold of high rate detection and providing an output signal when the input thereto exceeds said high limit, first bistable switch means responsive to said high limit circuit output signal for switching to a switched output state, second bistable switch means responsive to said low limit circuit output signal for switching to a switched output state, a first delay means for providing a first fixed delay of said first switched output state level, and a second delay means for providing a second different fixed delay of said second switched output state level, and means coupling either of said delayed level signals to said marking means for providing discernible marker pulses on said electrocardiogram corresponding to either of said high or low rate conditions.

8. The improvement of claim 7 wherein said high limit circuit output is a double pulse marker and said low limit circuit is a single pulse.

9. The improvement of claim 8 wherein said single and double pulse markers are transtelephonically transmittable to a remote detector.

10. A cardiac pacer including a monitoring system for automatically indicating a rate of pacer activity different from a predetermined rate comprising:
 (a) generating means responsive to both pacer EKG signals and cardiac EKG signals for generating corresponding pacer and cardiac pulse signals;
 (b) combining means responsive to said generating means for combining the pacer and cardiac pulse signals;
 (c) low limit detection means responsive to said combining means for producing a low limit pulse when the rate of the combined pacer and cardiac EKG signals falls below a predetermined low rate; and
 (d) indicator pulse generation means responsive to a low limit pulse from said low limit detection means for generating a distinguishable marker pulse signal for marking a low rate of pacer activity for later clinical EKG detection.

11. The cardiac pacer of claim 10 wherein said distinguishable marker pulse signal marking a low rate of pacer activity is a single pulse generated a predetermined period of time after a pacer pulse.

12. The cardiac pacer of claim 10 further comprising high limit detection means responsive to pacer pulse signals for generating a second distinguishable marker pulse signal for marking a high rate of pacer activity for later clinical EKG detection.

13. The cardiac pacer of claim 12 wherein said second distinguishable marker pulse signal for marking a high rate of pacer activity is a double pulse generated a predetermined period of time after a pacer pulse.

14. The cardiac pacer of claim 12 wherein said distinguishable marker pulse signal marking a low rate of pacer activity is a single pulse and said second distinguishable marker pulse signal marking a high rate of pacer activity is a double pulse, both said single pulse and the first of said double pulses being generated the same first predetermined period of time after a pacer pulse, and the second pulse of said double pulse being generated a second predetermined period of time after the first pulse of said double pulse.

15. The cardiac pacer of claim 14 wherein said first predetermined period of time is 120 milliseconds and said second predetermined period of time is 20 milliseconds.

* * * * *